United States Patent [19]

Lanier et al.

[11] Patent Number: 4,599,304
[45] Date of Patent: Jul. 8, 1986

[54] METHOD FOR MONITORING ACTIVATED CELL SUBPOPULATIONS

[75] Inventors: Lewis Lanier, Los Altos; Joseph Phillips, Redwood City, both of Calif.

[73] Assignee: Becton, Dickinson and Company, Franklin Lakes, N.J.

[21] Appl. No.: 539,876

[22] Filed: Oct. 7, 1983

[51] Int. Cl.$^4$ .................. G01N 33/53; A61K 39/00; A61K 45/02; C12N 15/00

[52] U.S. Cl. .......................... 435/7; 435/2; 435/4; 435/29; 435/948; 935/101; 935/108; 935/110; 436/548; 436/537; 424/85

[58] Field of Search .............. 436/63, 164, 172, 519, 436/807, 548, 537, 800; 422/52, 68; 356/39; 250/461.2; 935/110, 101; 424/85, 101; 435/2, 7, 29, 948

[56] References Cited

U.S. PATENT DOCUMENTS

| | | | |
|---|---|---|---|
| 4,284,412 | 8/1981 | Hansen | 356/39 |
| 4,492,752 | 1/1985 | Hoffman | 436/519 |
| 4,499,052 | 2/1985 | Fulwyler | 436/172 |

OTHER PUBLICATIONS

Lampson, L. A. et al., *J. Immunology*, vol. 125, No. 1, 1980, pp. 293-299.
Abo, T. et al., *J. Immunology*, vol. 129, No. 4, 1982, pp. 1752-1757.
Goto, M. et al., *J. Exp. Med.*, vol. 157, 1983, pp. 1309-1323.
Titus, J. A. et al., *J. Immunol. Meth.*, vol. 50, 1982, pp. 193-204.
Phillips, J. H. et al., J. Exp. Med., vol. 159, Apr. 1984, pp. 993-1008.
*Chemical Abstracts*, vol. 94, No. 13, 1981, abstract No. 101091b, Zarling, J. M. et al.
*Chemical Abstracts*, vol. 96, No. 21, 1982, abstract No. 179168z, Cantrell, D. A. et al.
Lanier, L. L. et al., *J. Immunol.*, vol. 132, No. 1, 1984, pp. 151-156.
Lanier, L. L. et al., *J. Immunol.*, vol. 131, No. 4, 1983, pp. 1789-1796.

*Primary Examiner*—Christine M. Nucker
*Assistant Examiner*—Jeremy M. Jay
*Attorney, Agent, or Firm*—James R. McBride

[57] ABSTRACT

A method of distinguishing multiple subpopulations of a cell sample whereby resting and activated human natural killer cells subpopulations can be monitored. This method utilizes two monoclonal antibodies identified as anti-Leu 11 and anti-DR (or anti-Leu 10 or anti-transferrin receptor).

7 Claims, 6 Drawing Figures

METHOD FOR MONITORING ACTIVATED CELL SUBPOPULATIONS

BACKGROUND OF THE INVENTION

1. Field of the Invention

The present invention relates to a method for distinguishing activated natural killer cells from resting, non-activated killer cells.

2. Description of the Prior Art

Considerable attention has recently been given to the study of cells from unimmunized hosts which are capable of lysing tumor cells in vitro. Such cells are commonly referred to as natural killer cells. Natural killer cells may play an important role in malignancy and disease. Essentially all natural killer cells present in human peripheral blood can be identified using the commercially available anti-Leu 11 monoclonal antibody. It is known that the use of certain cancer treatment agents, such as interferon, interferon-inducing agents, and interleukins, influence the number and potency of natural killer cells in human peripheral blood. Any process of influencing the number and potency of natural killer cells is referred to herein as "activation" of natural killer cells. These natural killer cells are referred to as "activated natural killer cells". Activated natural killer cells differ in functional properties from unactivated, resting natural killer cells. Human natural killer cells are known to express a variety of antigens, some of which are common to the T cell lineage and others to the myeloid cell lineage. Activated natural killer cells have increased levels of expression of certain cell surface antigens, such as DR, DS, and transferrin receptor.

It whould be desirable to provide a method whereby activated natural killer cells can be distinguished and enumerated separately from resting, non-activated natural killer cells, to permit monitoring of changes which may occur in natural killer cell populations during the development and treatment of disease.

SUMMARY OF THE INVENTION

In accordance with the present invention, a method is provided for distinguishing activated natural killer cells from resting, non-activated natural killer cells. In the method, a combination of monoclonal antibodies conjugated to different labels is used to identify and discriminate those natural killer cells which are activated from those which are not activated.

DEFINTIONS

Monoclonal Antibodies—A homogeneous antibody obtained from a continuous cell line which is usually produced by the fusion of mouse myeloma cells to spleen cells, first described by Kohler and Milstein (Nature, 256, 495–497, 1975). The specificity of a particular monoclonal antibody is influenced principally by the type of antigen employed to immunize the host and the selection technique used for isolating the hybrid cell (called "hybridomas"). It is now recognized that substantial functional equivalent monoclonal antibody for a particular monoclonal antibody can be provided by repetition of the immunization process with the same or related antigens.

FACS Cell Sorter—A fluorescence activated cell sorter, manufactured by Becton Dickinson FACS Systems, which is useful for detecting particles such as cells and the like. FACS apparatus commonly includes several detectors for the detection of subpopulations of cells in a mixture. For example, devices are known which include two fluorescent activated channels associated with the respective fluorescence detectors. In these devices, a fluorescence detector is used for each category of fluorochrome-treated cells to be detected in the mixture of cells in the sample being analyzed. In some cases, a separate light source is used to excite each different type of fluorochrome which has been bound onto a cell to be studied. Apparatus utilizing two light sources for analyzing an equivalent number of fluorochrome tagged particles are described in, for example, U.S. Pat. No. 4,284,412. Additional instrumentation utilizes mercury arc lamp sources for light excitation, such as in the FACS Analyzer, manufactured by Becton Dickinson FACS System.

Anti-Leu-11—A commercially available monoclonal antibody produced by immunization with large granular lymphocytes. Anti-Leu-11 is available in two forms, anti-Leu-11a and anti-Leu-11b, both forms are useful in the present invention and are referred to herein collectively as anti-Leu-11. Anti-Leu-11a (hybridoma clone NKP-15) was produced by immunization with large granular lymphocytes purified by percoll gradients (Pharmacia Fine Chemicals, Piscataway, N.J.). Anti-Leu-11b (hybridoma clone G022) was produced by immunization against granulocytes. Anti-Leu-11 reacts with from about 10% to 20% of the peripheral blood lymphocytes, essentially all natural killer cells in peripheral blood, and neutrophils. Anti-Leu-11 does not react with the eosinophil component of granulocutes. Anti-Leu-11 has strong Fab binding to the Fc receptor sites on large granular lymphocytes. Non-anti-Leu-11 monoclonal antibodies have the usual random Fc binding properties of monoclonal antibodies to Fc receptors on granulocytes. A monoclonal antibody which is functionally equivalent to anti-Leu-11, when reacted with granulocytes, or large granular lymphocytes will prevent any further substantial binding of IgG aggregates. IgG aggregates can be produced by binding fluorescein iso thiocyanate (FITC) to rabbit IgG and subjecting the labelled rabbit IgG to a temperature of 65° C. for one-half hour. A monoclonal antibody which is equivalent to anti-Leu-11 also can be recognized by reacting the suspected equivalent monoclonal antibody with large granular lymphocytes and subsequently reacting the treated large granular lymphocytes with commercially available anti-Leu-11. If the commercially available anti-Leu-11 does not react with the large granular lymphocytes, treated with the suspected equivalent monoclonal antibody, such monoclonal antibody is a substantial functional equivalent of anti-Leu-11.

Anti-DR—A commercially available monoclonal antibody secreted by clone L243, as described by Lampson and Levy, (Journal of Immunology, 125:293, 1980). This antibody recognizes a two-chain glycoprotein structure (28Kd–34Kd), known as DR antigen, which is present on resting human B cells and monocytes, and on activated T lymphocytes from all individuals. Any monoclonal antibody reacting with the DR antigen can be deemed anti-DR.

Anti-Leu-10—A commercially available monoconal antibody secreted by clone SK10. This monoclonal antibody recognizes a two-chain glycoprotein structure (27, 32Kd), known as DS. This antigen is present on resting B cells, activated T cells, and in low levels on monocytes. It is present on the cells of most individuals, but absent from DR7 homozygous individuals. Any monoclonal antibody reacting with the DS antigen can be deemed anti-DS.

Anti-Transferrin Receptor—A commercially avaiable monoclonal antibody secreted by clone L01. This antibody recognizes a two-chain glycoprotein homodimer structure (180Kd unreduced). This structure specifically binds iron-saturated human transferrin. Transferrin receptor is present in low levels of leukocytes, but in high levels on all mitogen or alloantigen activated lymphoblasts, tumor cells, and monocytes. Any monoclonal antibody which reacts with this transferrin receptor can be deemed anti-transferrin receptor.

DETAILS OF THE INVENTION

Figure 1:
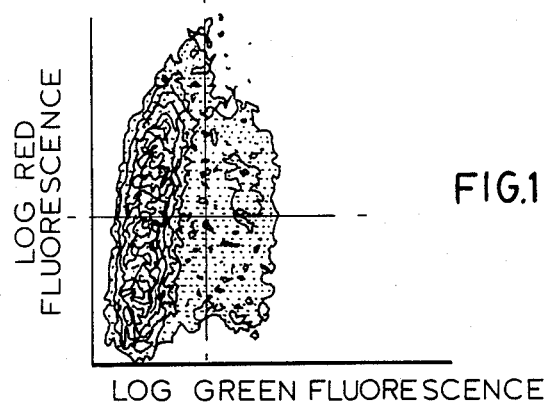
FIGS. 1 through 6 are contour plots produced by two color flow cytometry apparatus illustrating various features of the invention.

In the method, human cells from a sample (either whole blood, the mononuclear cell fraction of whole blood, or cells from other human tissues) are first reacted with a first monoclonal antibody which has been conjugated with a first fluorochrome label. The first monoconal antibody is selected to react with substantially all natural killer cells, whether activated or non-activated. Anti-Leu-11 is suitable for use as the first monoclonal antibody. The sample is then reacted with a second monoclonal antibody which have been conjugated with a second fluorochrome label which can be distinguished from the first fluorochrome label. Monoclonal antibodies which detect DR, DS, or transferrin receptor are suitable for use as the second antibody. These antigens do not appear, or appear only in low levels on non-activated natural killer cells. However, they can be detected on natural killer cells (as well as T cells) which have become "activated". Therefore, in this method the combined use of a first monoclonal antibody, such as anti-Leu-11 and a second monoclonal antibody selected from anti-DR, anti-Leu 10 (a monoclonal antibody which detects DS), anti-transferrin receptor or combinations thereof permits identification of activated natural killer cells in a heterogeneous cell population containing resting or non-activated natural killer cells. It should be understood that the antibody preparation used to identify natural killer cells may be a single antibody or a combination of several antibodies having the desired specificity. Similarly, the antibody preparation used to identify activated cells may be a single antibody or a combination of antibodies having the desired specificity.

The cells which have been reacted with the first and second monoclonal antibody are identified by a suitable detection method such as examination with a fluorescence microscope or through use of a flow cytometer using well known techniques. The fluorescence emitted by the excited fluorochromes is detected and subpopulations of the cells are distinguished based on the detected fluorescence of the first fluorochrome and the second fluorochrome. Through suitable selection of the fluorochromes, the relative proportions of non-activated and activated natural killer cells can be monitored.

By examining the peripheral blood of a patient on a periodic basis, while the patient is undergoing treatment, the natural killer cell subpopulations can be monitored to provide information concerning the effectiveness of the treatment. In addition the method can be used for diagnostic screening to provide information concerning the immune status of an individual.

It should be understood that various pairings of fluorochromes can be used as the first and second fluorochrome. In general, it is only necessary that the first and second fluorochrome have detectable emission difference. Potential pairs of fluorochromes include fluorescein or rhodamine as the first fluorochrome and phycoerythrin or Texas Red as the second fluorochrome. In addition, different phycobiliprotein compounds can be used as both the first and second fluorochromes. Fluorescence excitation of fluorescein or phycoerythrin can be achieved using the 488 nm line of an argon laser. Texas-Red can be excited using the 568 nm line of a krypton laser or by using rhodamine 6G dye lasers with excitation around 600 nm.

Natural killer cells are mononuclear cells, In a preferred embodiment of the invention, the monoclonal cells are separated from the other cells in the blood sample by the Ficoll-Hypaque or similar separation technique to provide a mononuclear cell fraction. The mononuclear cell fraction is then reacted with the first and second labelled monoclonal antibodies as previously described. It should also be understood that the separation of the mononuclear cell fraction from the total lymphocyte fraction need not be effected. The total lymphocyte fraction, for example, can be reacted with the first and second antibodies and analyzed with a flow cytometry apparatus. The mononuclear cell fraction is recognized the the flow cytometer apparatus on the basis of other biophysical properties of such cells including volume and light scatter. The mononuclear cells are detected in an unseparated blood sample using appropriate instrumentation such as a FACS Analyzer or FACS.

In a preferred embodiment of the invention, anti-Leu-11 is used as the first monoclonal antibody; Anti-DR, anti-Leu-10 anti-transferrin receptor or combinations thereof is used as the second monoclonal antibody and phycoerythrin-B and FITC are used as the pair of fluorochromes.

The following example further illustrates various features of the invention but is not intended to limit the scope of the invention as set forth.

EXAMPLE

1. Cell Preparation

Human peripheral blood was collected into sodium heparin coated 15 ml tubes. The blood was diluted 1:1 with phosphate buffered saline (0.1M phosphate, pH 7.3). Fifteen ml of Ficoll-Paque (Pharmacia Fine Chemicals, Piscataway, N.J.) was added to a 50 ml conical centrifuge tube and the blood was gently layered onto the Ficoll-Paque. This was centrifuged at 570×g for 45 min. at room temperature in a swinging bucket rotor. After centrifugation, the mononuclear fraction containing the lymphocytes was removed from the interface of the gradient. These cells were washed twice in 50 ml phosphate buffered saline and were adjusted to a concentration of $2\times10^7$/ml in phosphate buffered saline containing 0.1% sodium azide.

For examination of "unactivated" natural killer cells, these mononuclear cells were immediately stained as described below. In order to "activate" the natural killer cells within this population, these lymphocytes were placed into culture in the presence of an allogeneic human lymphoblastoid cell line (such as SB) for 5 days. In a typical assay, mononuclear cells ($1\times10^5$ cells/ml in RPMI-1640+10% serum) were cultured in the presence of an equal number of foreign stimulator cells (e.g. a tumor cell line from another individual at $1\times10^5$ cells/ml in RPMI-1640+10% serum). The stimulator cells were either irradiated or pre-treated with mitomycin C to prevent them from reacting with the effector cells. After 5 days of culture at 37° in a humidified $CO_2$ (5%) incubator, the cells were harvested, washed, and stained as described below.

2. 2 Color Immunofluorescence Staining

Anti-DR, anti-Leu 10 (DC) and anti-Leu 11 prepared at the Becton Dickinson Monoclonal Center, Inc., Mountain View, CA were used for this example. All antibodies were purified by routine and standard antibody purification techniques. Fluorescein isothiocyanate (FITC), or phycoerythrin-B was conjugated to the antibodies by standard methods.

One million mononuclear leukocytes in a total volume of 50 microliters diluent were placed into a 12×75 mm polystyrene tube. One microgram of fluorescein (FITC) conjugated anti-Leu 11 in 10 microliters diluent was added to each tube. The tubes were vortexed, and after 15 minutes, 3 ml diluent were added to each tube and the samples were centrifuged at 400×g for 5 minutes. The supernatant was removed and one microgram of phycoerythrin-B conjugated anti-DR or phycoerythrin-B conjugated anti-Leu 10 in a total volume of 10 microliters diluent were added to each tube. The samples were vortexed and incubated for an additional 15 minutes. The cells were washed twice in 1 ml diluent, the supernatant was removed and the cell pellet was resuspended in a 1% paraformaldehyde/0.85% saline solution. The fixed cells were stored at 4° C. in the dark until analysis. All dilutions and cell washing were performed in cold phosphate buffered saline (0.1M phosphate, pH 7.2) contained 0.1% sodium azide and all procedures were carried out at 4° C.

3. Detection

Dead cells, erythrocytes, granulocytes, monocytes and platelets were excluded from analysis by setting an appropriate threshold trigger on the low forward angle and 90 degree light scatter parameters. Low angle forward light scatter, 90 degree light scatter, green fluorescence, and the red fluorescence were stored in list mode using a Consort 40 PDP/11 based computer system (Becton Dickinson FACS Division, Sunnyvale, CA). Single parameter data were displayed as histograms with fluorescence channel on the x-axis and relative number of cells on the y-axis. In determining the % positive cells, a cell marker was set so that 5% or less of the cells were to the right of this channel marker. Using this as a reference point, the % of cells in the specific antibody which were labeled in stained sample histogram was calculated. The control % was then substracted from this value.

Essentially identical procedures for gating and analysis were used with the FACS analyzer with Consort 20 or 30 Computer Systems except that light excitation was provided by mercury arc lamp, and volume and 90° light scatter were used for gating.

Two parameter data were collected into a 64×64 matrix and displayed as contour map. "Contours" were drawn to indicate increasing numbers of cells in a defined area of the array as described hereinbelow in a discussion of the FIGURE.

4. Description of Figure

Figure 2:
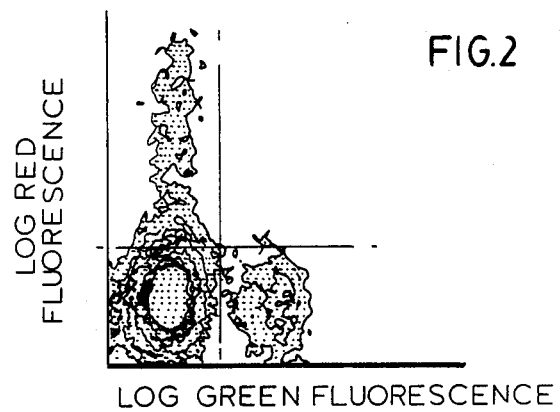
Figure 3:
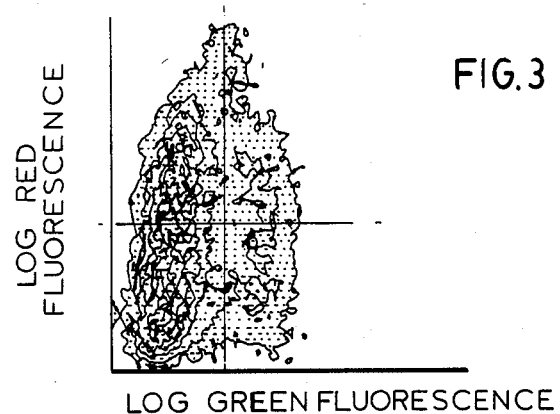
Figure 4:
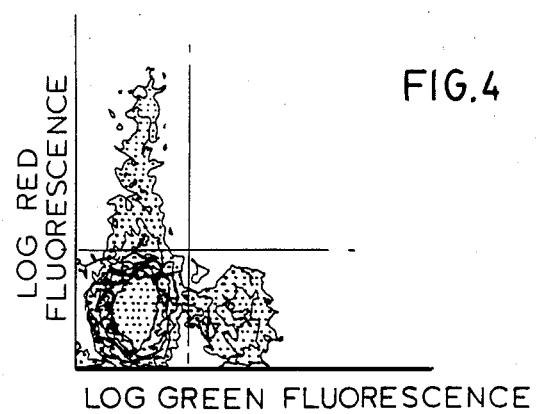
Figure 5:
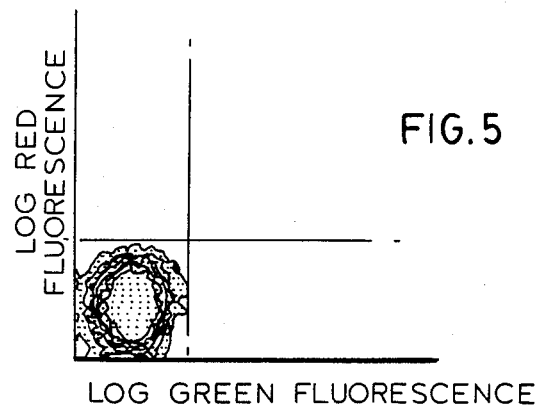
Figure 6:
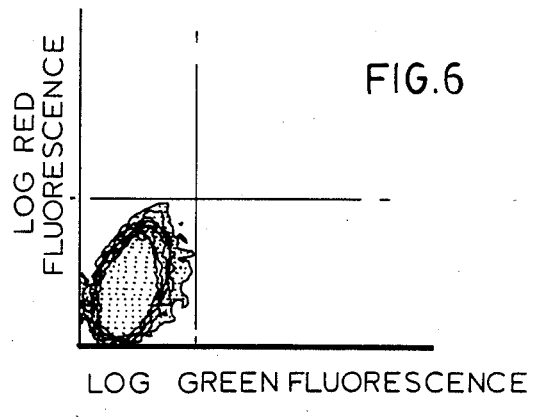

Unstimulated mononuclear cells prepared from human peripheral blood, and mononuclear cells activated by incubation for 5 days in the presence of mitomycin C treated SB tumor cells, as described above, were reacted with the first and second antibody and subjected to analysis is a FACS IV to generate the plots shown in FIGS. 1-6. FIG. 1 shows activated cells and FIG. 2 shows unactivated cells stained with FITC anti-Leu 11 and PE-anti-DR. FIG. 3 shows activated cells and FIG. 4 shows unactivated cells stained with FITC anti-Leu 11 and PE anti-Leu 10 (DC). FIG. 5 shows activated cells and FIG. 6 shos unactivated cells which are not reacted with the first and second antibody (unstained control cells).

Samples were analyzed using a FACS IV by standard methods. The cells were "gated" on the bais of low forward angle and 90° light scatter. The data are presented as contours of green (x-axis) and red (y-axis) fluorescence. Concentric contours were drawn to enclose areas containing more than 5-100 cells. Approximately 20,000 cells were analyzed in each sample. In each contour map, perpendicular lines have been drawn to define the 4 quadrants containing the various cells of interest:

Lower left: unlabeled cells
Upper left: cells labeled only with PE conjugated antibodies Lower right: cells labeled only with FITC conjugated antibodies Upper right: cells labeled with both FITC and PE conjugated antibodies Note that in the unstimulated lymphocyte population few cells co-express Leu 11 and DR or DC (i.e. cells with both red and greem specific fluorescence. In contrast, natural killer cells which have undergone activation co-express Leu 11 and DR or DC.

What is claimed is:

1. A method for monitoring activated and non-activated natural killer cell subpopulations comprising:
   (a) providing a sample of cells containing a population of natural killer cells;
   (b) labelling selected cells of said sample with a first monoclonal antibody(s) coupled with a first fluorochrome label;
   (c) labelling selected cells of said sample with a second monoclonal antibody(s) coupled with a second fluorochrome label said first fluorochrome label and said second fluorochrome label having a detectable emission difference; one of said first or second monoclonal antibodies being anti-Leu 11 and the other of said first or second monoclonal antibodies being selected from the group consisting of anti-DR, anti-Leu 10 and anti-transferrin receptor;
   (d) providing excitation energy to excite said first fluorochrome label and said second fluorochrome label;
   (e) detecting the fluorescence emitted by the excited fluorochromes; and
   (f) distinguishing subpopulations of activated and non-activated natural killer cells relative to the detected fluorescence characteristics thereof, whereby the relative proportion of non-activated and activated natural killer cells can be monitored.

2. A method in accordance with claim 1 wherein said sample of cells is a peripheral blood sample.

3. A method in accordance with claim 2 wherein said blood sample is treated to provide a mononuclear cell fraction comprising substantially all of the lymphocytes including natural cells prior to step (b) of claim 1.

4. A method in accordance with claim 1 wherein said first fluorochrome label is selected from fluoroscein, rhodamine and a phycobiliprotein and said second fluorochrome is selected from Texas Red and a phycobiliprotein.

5. A method in accordance with claim 1 wherein said first fluorochrome is fluorescein and said second fluorochrome is phycoerythrin.

6. A method in accordance with claim 1 wherein said fluorescence detection is accomplished by means of a fluorescence microscope.

7. A method in accordance with claim 1 wherein said fluorescence is accomplished with a fluorescence activated cell sorter.

* * * * *